United States Patent [19]
Plantema

[11] 4,117,246
[45] Sep. 26, 1978

[54] PROCESS FOR PREPARING A CYCLOALKANOL

[75] Inventor: Otto G. Plantema, Geleen, Netherlands

[73] Assignee: Stamicarbon, B.V., Geleen, Netherlands

[21] Appl. No.: 859,191

[22] Filed: Dec. 9, 1977

[30] Foreign Application Priority Data

Dec. 16, 1976 [NL] Netherlands .......................... 7613947

[51] Int. Cl.² ............................................. C07C 29/06
[52] U.S. Cl. .................................... 568/821; 568/835
[58] Field of Search ........... 260/617 M, 639 R, 631 R

[56] References Cited
U.S. PATENT DOCUMENTS

| | | | |
|---|---|---|---|
| 2,042,212 | 5/1936 | Deanesly | 260/639 R |
| 2,504,517 | 4/1950 | Greene | 260/631 R |
| 3,374,261 | 3/1968 | Lloyd et al. | 260/617 M |

*Primary Examiner*—Joseph E. Evans
*Attorney, Agent, or Firm*—Cushman, Darby & Cushman

[57] ABSTRACT

A process for the preparation of cycloalkanol by way of a two stage reaction from cycloalkene. The first reaction stage consists of reacting cycloalkene with sulphuric acid. The resultant adduct which is cycloalkyl hydrogen sulphate is separated from the reaction mixture by use of an inert solvent. The adduct is then hydrolyzed in the second reaction stage to product the cycloalkanol.

20 Claims, 1 Drawing Figure

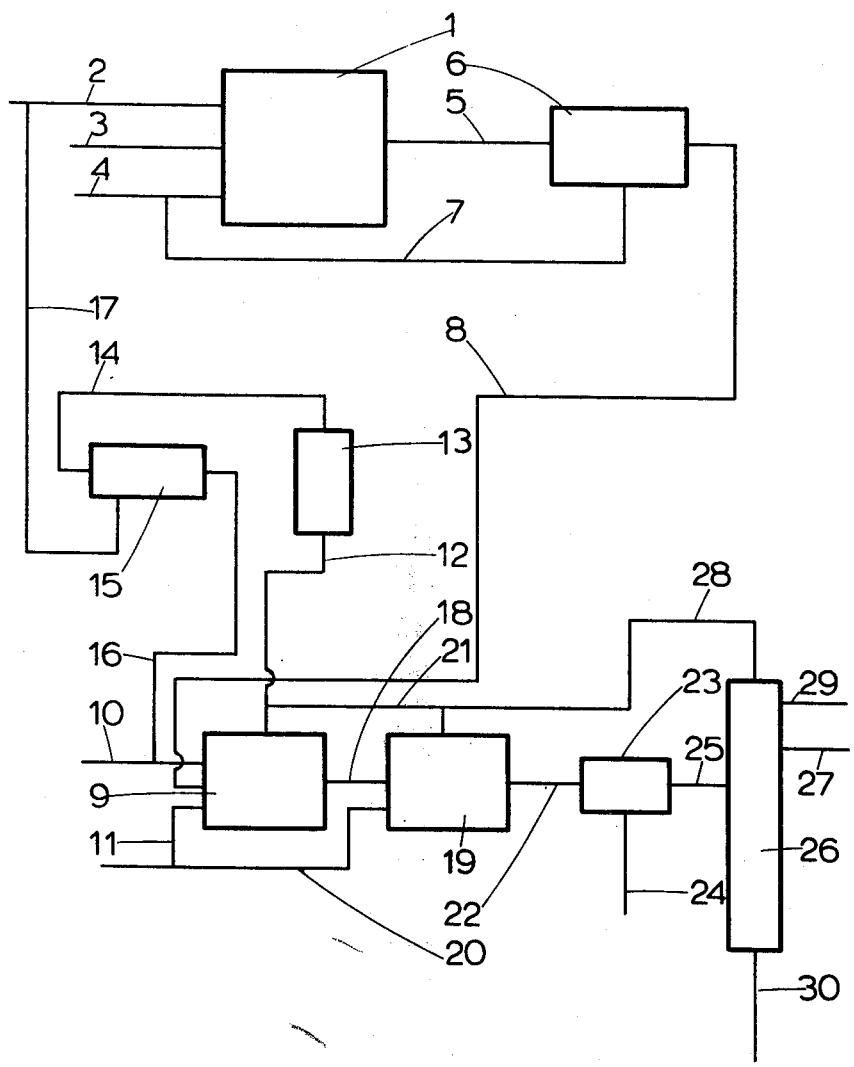

PROCESS FOR PREPARING A CYCLOALKANOL

BACKGROUND OF THE INVENTION

The invention is directed to a process for the preparation of a cycloalkanol which is carried out in a two stage reaction. In the first reaction stage, a cycloalkene is reacted with sulphuric acid, and in the second reaction stage the resulting adduct which is a cycloalkyl hydrogen sulphate is hydrolyzed to form the cycloalkanol. Although the process according to the invention can be used for preparing any cycloalkanol, especially those with 5–12 carbon atoms in the ring, the invention relates in particular to a process for the preparation of cyclododecanol from cyclododecene.

A process of this type is disclosed in the French Patent Specification 1,407,202. In that process the reaction mixture of the first stage which has present cyclododecyl hydrogen sulphate as the adduct is poured into water or onto ice at a temperature which is not higher than 0° C., while being vigorously stirred. The hydrolysis to cyclodecanol of the cyclododecyl hydrogen sulphate is then completed by heating the resultant reaction mixture to a temperature of about 100° C.

But that process has serious disadvantages including the fact that the amount of water or ice required in the second reaction stage is about 6 kg. per kg. of sulphuric acid used in the first reaction stage. Another disadvantage is that when the reaction mixture of the first reaction stage is added to the water or ice, a large amount of heat is evolved which then must be removed to keep the reaction mixture at 0° C. This cooling is extremely expensive. A further disadvantage is that a large amount of dilute sulphuric acid is obtained as an undesired by-product which must necessarily then be removed from the process.

DESCRIPTION OF THE INVENTION

It is therefore an objective of the present invention to provide a process which overcomes all of these disadvantages and to utilize the available energy in the most efficient manner in the accomplishment of said objective.

According to applicants' process a cycloalkanol is prepared by first reacting a cycloalkene with sulphuric acid. After reacting the cycloalkene with sulphuric acid, the resultant cycloalkyl hydrogen sulphate is separated from the reaction mixture which is comprised of the cycloalkyl hydrogen sulphate, unreacted cycloalkene and sulphuric acid, by using an inert solvent which forms a solution with the cycloalkyl hydrogen sulphate and the unreacted cycloalkene. This effects a zone separation into a plurality of layers consisting essentially of a sulphuric acid layer and a solvent layer. The solvent layer is comprised of the inert solvent, the cycloalkyl hydrogen sulphate and the unreacted cycloalkene. The layers are then separated and the cycloalkyl hydrogen sulphate in the solvent layer is hydrolyzed to produce the cycloalkanol.

Applicants' process eliminates the disadvantages discussed above. The amount of water or other aqueous liquid used in the second reaction stage is much smaller being in the range of about 2 kg. of water per kg. of sulphuric acid used in the first reaction stage. The layer comprising the solvent and the cycloalkyl hydrogen sulphate of the reaction mixture of the first reaction stage is virtually free of uncombined sulphuric acid. This means that the evolution of heat in the second stage is reduced considerably. Also the amount of undesired dilute sulphuric acid formed is much smaller. Furthermore, applicants' process makes it possible to effect the hydrolysis of cyclododecyl hydrogen sulphate with a basic liquid without excessive decomposition of cyclododeca products into undesirable by-products. This makes it possible to utilize the heat of neutralization which is evolved through the use of a basic liquid and, which would otherwise be lost to evaporate the solvent from the second reaction stage mixture.

The solvent used in separating the first reaction stage mixture into a sulphuric acid layer and a solvent layer may be added, if desired, after completion of the first reaction stage. But, preferably, the solvent is already present during the first reaction stage. One advantage of having the solvent present during the first reaction stage is that the viscosity of the first reaction stage is thereby lowered so that stirring in the first reaction stage is accomplished with less energy.

The inert solvent used in the instant process preferably has a boiling point at atmospheric pressure of no higher than about 150° C. The distribution coefficient of the cycloalkyl hydrogen sulphate between the solvent and sulphuric acid should amount to about at least 1 to 1 and preferably to at least about 5 to 1.

Examples of suitable inert solvents are halogenated hydrocarbons with, preferably, no more than 6 hydrocarbons per molecule. Most preferred are chlorinated hydrocarbons, particularly methylene chloride, chloroform, tetrachloromethane, 1,2-dichlorethane, trichlorethene, and 1,1,1-trichlorethane, or mixtures of two or more of these substances. Brominated hydrocarbons, e.g., 1,2-dibromethane, may also be used as well as fluorinated hydrocarbons or hydrocarbons containing more than one type of halogen as a substituent. Other polar solvents may also be used such as mono- and polyfunctional ethers; e.g., diethyl ether, diisopropyl ether, diamyl ether, dioxane, and the dimethyl ether of diethylene glycol; sulphones, e.g., dipropyl sulphone and sulpholane; and sulphoxides, e.g., dimethyl sulphoxide. Inert hydrocarbons with, preferably, no more than 12 carbon atoms, e.g., gasoline, toluene, or xylene can also be used.

The weight ratio of solvent to sulphuric acid ranges between from about 1:20 and 5:1. Higher ratios of solvent to sulphuric acid are possible, but are less attractive economically.

Applicants' process is especially suited to the preparation of cycloalkanols containing 8 or more carbon atoms in the ring. The distribution coefficients of the cycloalkyl hydrogen sulphates containing 8 or more carbon atoms in the ring between the inert solvent and the sulphuric acid are higher than the distribution coefficients of the cycloalkyl hydrogen sulphates with less than eight carbon atoms in the ring. This means that relatively less solvent is needed when preparing cycloalkanols containing 8 or more carbon atoms in the ring than when preparing cycloalkanols containing less than 8 atoms in the ring, and that therefore, the weight ratio of solvent to sulphuric acid can be lower when producing cycloalkanols containing 8 or more carbon atoms in the ring than when producing cycloalkanols containing less than 8 carbon atoms.

The first reaction stage of reacting the cycloalkene with sulphuric acid whether or not done in the presence of the solvent is effected with at least 0.8 moles of sulphuric acid per mole of cycloalkene and preferably with an amount of sulphuric acid in the range of about 1.0 to about 5.0 moles of sulphuric acid per mole of cycloalkene with the best results obtained when using about 1.5 to 2 moles of sulphuric acid per mole of cycloalkene. A greater excess of sulphuric acid may be used but it offers no advantages. The cycloalkene may be the pure cycloalkene or the cycloalkene mixed with other components, especially a cyclododecene product obtained by hydrogenation of cyclododecatriene and containing, in addition to cyclododecene, minor amounts of cyclododecane and, also possibly, cyclododecadiene and/or cyclododecatriene. The sulphuric acid used should preferably have a concentration of at least about 85% by weight, 96–98% and higher by weight sulphuric acid being particularly suitable. The reaction temperature in the first reaction stage usually ranges between about −50° C. and about +30° C. with a preferred range between about −20° C. and 0° C. with the best results obtained in the range of about −10° C. and about 15° C.

After completion of the first reaction stage which is the reaction between the cycloalkene and sulphuric acid, the solvent, if not yet present, is added and the layer of sulphuric acid is separated off. This sulphuric acid layer will contain only a little of the organic material and can be returned to the first reaction stage. This makes it possible to considerably reduce the consumption of sulphuric acid, which is another important advantage of applicants' process.

The solvent layer containing the cycloalkyl hydrogen sulphate and unreacted cycloalkene is then subjected to a hydrolysis with an aqueous liquid in the second reaction stage. The aqueous liquid may be, for example, water or a basic solution such as aqueous sodium hydroxide, potassium hydroxide, or preferably, aqueous ammonia. It is also possible to separately add water and gaseous ammonia. The second reaction stage may be carried out at temperatures ranging between about −20° and about 200° C., but is preferably carried out at temperatures ranging between about 50° to about 150° C. with the best results obtained at temperatures ranging between about 80° C. and about 120° C. The pressure may be atmospheric, although if so desired, the process may be carried out at reduced or elevated pressure with the pressure being in the range of from about 0.1 atm. to about 10 atm. Preferably, the reaction heat evolved in the second reaction stage is removed, at least in part, by evaporation of the inert solvent and/or unreacted cycloalkene. Because the solvent and unreacted cycloalkene must be separated from the cycloalkanol by evaporation, utilization of the evolved reaction heat for this purpose constitutes a considerable saving of energy which is another important advantage of applicants' process. The evaporated solvent and unreacted cycloalkene after being condensed or dried may be returned to the first reaction stage.

In a preferred embodiment of applicants' process, the second reaction stage is effected in two steps. In the first step the solvent layer is contacted with water, and, if so desired, a base, in particular ammonia, while maintaining the pH of the resultant aqueous liquid below 1. In the second step the resultant aqueous liquid is neutralized until a pH over 1. The greater part of the cycloalkyl hydrogen sulphate is hydrolyzed to the cycloalkanol in the first step at a low pH where the hydrolysis reaction proceeds quickly. In the second step ammonium sulphate, for instance, is formed which can be sold as a fertilizer. The heat of neutralization in the second step can be utilized for evaporation of any inert solvent and/or unreacted cycloalkene still present.

DESCRIPTION OF THE DRAWINGS

By way of example, the invention will be illustrated by reference to the drawing.

Reaction vessel 1 which is provided with means for stirring and means for cooling is fed with (a) chloroform through conduit 2, (b) a mixture of 95% by weight of cyclododecene and 5% by weight of cyclododecane obtained by hydrogenation of cyclododecatriene through conduit 3, and (c) sulphuric acid with a concentration of 98% by weight through conduit 4. The contents of vessel 1 are stirred vigorously, while the temperature in vessel 1 is maintained between about −20° C. and about −10° C. The retention time in the vessel is about 10 minutes.

The reaction mixture flows from vessel 1 through conduit 5 to separator 6. Here the reaction mixture separates into (a) a bottom layer consisting almost exclusively of sulphuric acid which is returned through conduit 7 to conduit 4 and thus to reaction vessel 1, and into (b) a top layer substantially comprising of a solution of cyclododecyl hydrogen sulphate in chloroform with cyclododecane and some by-product as impurities.

Said top layer is passed under pressure through conduit 8 to hydrolysis vessel 9 which is a pressure vessel. Vessel 9 is fed with water through conduit 10 and with gaseous ammonia through conduit 11. The amount of ammonia fed in is controlled so that the acid concentration in vessel 9 does not fall below 0.1 N free acid. The temperature in vessel 9 is maintained at about 100° C. The pressure in vessel 9 is equal to the autogenous pressure. The retention time in vessel 9 is about 60 minutes. Chloroform vapor containing water vapor exits vessel 9 through conduit 12 and is passed to condenser 13 and is condensed. The condensate is then passed through conduit 14 to water separator 15. There the water is separated out as the top layer and is passed through conduit 16 to conduit 10 and thus back to hydrolysis vessel 9. The layer of chloroform which is the bottom layer in water separator 15 and which still contains about 0.25% by weight of water is returned through conduit 17 to conduit 2 and thus to reaction vessel 1.

The reaction mixture flows from the hydrolysis vessel 9 through conduit 18 to the neutralization vessel 19 which is a pressure vessel. Enough gaseous ammonia is fed to vessel 19 through conduit 20 to convert all of the sulphuric acid into ammonium sulphate. Water is fed to the system through conduit 10 and the amount so fed is controlled so that a 40% by weight aqueous ammonium-sulphate solution is formed in vessel 19. The temperature in vessel 19 is maintained at about 100° C. and its pressure is equal to the autogenous pressure. Retention time in vessel 19 is about 10 minutes. Chloroform vapor is discharged from vessel 19 through conduit 21 and is passed to conduit 12 and then to the condenser 13 and treated further as described above.

The reaction mixture flows from neutralization vessel 19 through conduit 22 to separator 23 where the mixture is separated into an aqueous ammonium sulphate layer and a cyclododecanol layer which contains only minor amounts of chloroform and some cyclododecane, water and some by-product. The aqueous ammonium sulphate layer is discharged through conduit 24 and is processed for pure crystalline ammonium sulphate. The cyclododecanol layer flows through conduit 25 to distilling unit 26, where pure cyclododecanol is separated and recovered through conduit 27. A gaseous mixture of water and chloroform is discharged from the distilling unit 27 through conduit 28 to conduit 21 and is passed to conduit 1 and then to the condenser 13 and treated further as described above. Cyclododecane which was in the starting cyclododecene as an impurity is recovered through conduit 29. An organic distillation residue leaves the system through conduit 30.

Cyclohexene can be converted into cyclohexanol or cyclo-octene into cyclo-octanol in an analogous way.

The invention is further illustrated by reference to the following non-restrictive examples.

EXAMPLE I 30.6 grams of sulphuric acid (96% by weight, 0.306 mole) and 60 ml of $CHCl_3$ are put in 0.5-liter reactor and cooled to $-15°$ C.

Over a 15 minute period 33.25 grams of a mixture of cyclododecene (29.55 grams, 0.178 mole) and cyclododecane (3.70 grams, 0.022 mole) were added dropwise with vigorous mechanical stirring. The molar ratio between sulphuric acid and cyclododecene was 1.72. The temperature of the reaction mixture was maintained at $-15°$ C. by cooling. The reaction mixture was stirred at the same temperature for an additional 15 minutes and then pressed into a separator. The sulphuric acid layer (bottom layer) was separated off and analyzed and was found to contain less than 0.2 grams of organic material.

The chloroform layer (top layer) was diluted at 5° C. with 200 ml of water and then passed to the heated hydrolysis vessel where chloroform was distilled off. Next, the reaction mixture was heated at 95°–100° C. in this vessel for 60 minutes. The organic layer was separated off and analyzed. It was found to contain 3.52 grams of cyclododecane, 6.80 grams of cyclododecene (conversion 77%) and 23.45 grams of cyclododecanol (0.121 mole; yield 93%, calculated with subtraction of recovered starting material).

EXAMPLE II

The procedure of Example I was followed, but a molar ratio between sulphuric acid and cyclododecene of 1.15 was used. The conversion of cyclododecene was found to be 60%; the yield of cyclododecanol was 87%.

EXAMPLE III

The procedure of Example I was followed, but a molar ratio between sulphuric acid and cyclododecene of 2.30 was used. The conversion of cyclododecene amounted to 80%; the yield of cyclododecanol was 89%.

EXAMPLE IV

The procedure of Example I was followed, but the reaction temperature in the reactor was 0° C. The cyclododecene conversion amounted to 71%; the yield of cyclododecanol was 78%.

EXAMPLE V

The procedure of Example I was followed, but the layer of chloroform with the reaction product cyclododecyl hydrogen sulphate separated off was passed directly into the heated hydrolysis vessel. After the chloroform had been removed by evaporation, heating was continued at 95°–100° C. for 60 minutes. The organic layer was separated off and analyzed. The conversion of cyclododecene amounted to 77%; the yield of cyclododecanol was 90%.

EXAMPLE VI 17.25 grams of cyclohexene (95% pure; 0.200 mole) was added dropwise at 0° C. to a mixture of 30.6 grams of sulphuric acid (96% by weight; 0.306 mole), 0.1 gram of iron (II) sulphate and 60 ml of chloroform in the same manner as in Example I. The layer of sulphuric acid was separated off and extracted twice with 20 ml of chloroform. The three organic fractions were combined and diluted with 200 ml of water and were passed to the hydrolysis vessel. The chloroform and the cyclohexene that had not reacted were distilled off. After hydrolysis at 100° C. for 60 minutes, the distillate and the organic layer were analyzed. Together they contained 6.54 grams of cyclohexene (conversion 60%) and 11.04 grams of cyclohexanol (0.110 mole; yield 92% with subtraction of recovered cyclohexene).

Various modifications of the process of the invention may be made without departing from the spirit and scope thereof and it should be understood that the invention is intended to be limited only as defined in the appended claims.

What is claimed is:

1. Process for preparing cycloalkanol from a cycloalkene, which process comprises the steps of,
    (A) reacting a cycloalkene with sulphuric acid to form a reaction mixture consisting essentially of the corresponding cycloalkyl hydrogen sulphate, unreacted sulphuric acid, and unreacted cycloalkene;
    (B) providing an inert solvent to said reaction mixture of step (A) to effect a zone separation into a plurality of layers wherein one layer consists essentially of sulphuric acid, and a second layer consists essentially of said inert solvent, said cycloalkyl hydrogen sulphate, and said unreacted cycloalkene;
    (C) separating said layer of step (B) which consists essentially of said inert solvent, said cycloalkyl hydrogen sulphate, and said unreacted cycloalkene from the other layers of step (B), and thereafter;
    (D) hydrolyzing said separated layer of step (C) to form the cycloalkanol.

2. The process of claim 1, wherein the inert solvent is a halogenated hydrocarbon.

3. The process of claim 2, wherein the halogenated hydrocarbon is methylene chloride, chloroform, tetrachloromethane, 1,2-dichlorethane, trichlorethene, 1,1,1-trichlorethane, or mixtures thereof.

4. The process of claim 1, wherein the inert solvent has a boiling point at atmospheric pressure less than about 150° C.

5. The process of claim 1, wherein the sulphuric acid layer of step (B) is recycled to step (A).

6. The process of claim 1, wherein the hydrolyzing of step (D) consists essentially of the reaction of said adduct of step (A) and an aqueous liquid with heat being evolved and the temperature of the said reaction ranging from about 50° to about 150° C.

7. The process of claim 6, wherein said evolved heat is removed in the evaporation of said inert solvent and said unreacted cycloalkene.

8. The process of claim 6, wherein said aqueous liquid is basic and said heat evolved is the heat of neutralization, and is removed in the vaporation of said inert solvent and said unreacted cycloalkene.

9. The process of claim 6, wherein step (D) is effected in a first sub-step with water and optionally an alkaline liquid, whereby the pH of the aqueous mixture is kept below 1, and a second sub-step wherein the aqueous liquid is neutralized until a pH over 1.

10. The process of claim 1, wherein the reaction of step (A) is conducted in the presence of the inert solvent.

11. The process of claim 1, wherein the cycloalkanol is cyclododecanol and the cycloalkene is cyclododecene.

12. The process of claim 5, wherein said inert solvent is present during the reaction of step (A).

13. The process of claim 12, wherein said inert solvent is a halogenated hydrocarbon.

14. The process of claim 13, wherein the hydrolyzing of step (D) consists essentially of the reaction of said adduct of step (A) and an aqueous liquid with heat being evolved and the temperature of said reaction ranging from about 50° to about 150° C.

15. The process of claim 14, wherein said evolved heat is removed in the evaporation of said inert solvent and said unreacted cycloalkene.

16. The process of claim 15, wherein said aqueous liquid is basic and said heat evolved is the heat of neutralization and is removed in the evaporation of said inert solvent and said unreacted cycloalkene.

17. The process of claim 16, wherein the cycloalkanol is cyclododecanol and the cycloalkene is cyclododecene.

18. The process of claim 17, wherein said halogenated hydrocarbon is methylene chloride, chloroform, tetrachloromethane, 1,2-dichlorethane, trichlorethene, 1,1,1-trichlorethane, or mixtures thereof.

19. The process of claim 17, wherein the halogenated hydrocarbon has a boiling point at atmospheric pressure less than about 150° C.

20. The process of claim 13, wherein step (D) is effected in a first sub-step with water and optionally an alkaline liquid, whereby the pH of the aqueous mixture is kept below 1, and a second sub-step wherein the aqueous liquid is neutralized until a pH over 1.

* * * * *